(12) United States Patent
Huang et al.

(10) Patent No.: US 9,404,884 B2
(45) Date of Patent: Aug. 2, 2016

(54) BIOSENSOR DEVICE AND RELATED METHOD

(71) Applicant: Taiwan Semiconductor Manufacturing Company Limited, Hsin-Chu (TW)

(72) Inventors: Jui-Cheng Huang, Hsinchu (TW); Chin-Hua Wen, Toufen Township (TW); Tung-Tsun Chen, Hsinchu (TW)

(73) Assignee: Taiwan Semiconductor Manufacturing Company Limited, Hsin-Chu (TW)

( * ) Notice: Subject to any disclaimer, the term of this patent is extended or adjusted under 35 U.S.C. 154(b) by 17 days.

(21) Appl. No.: 14/261,477

(22) Filed: Apr. 25, 2014

(65) Prior Publication Data

US 2015/0308974 A1 Oct. 29, 2015

(51) Int. Cl.
*G01N 27/414* (2006.01)
*G01N 27/333* (2006.01)

(52) U.S. Cl.
CPC .................................. *G01N 27/333* (2013.01)

(58) Field of Classification Search
CPC ............... H01L 29/7816; H01L 29/66681; H01L 29/7835; H01L 29/66659; H01L 29/1083; H01L 29/1095; H01L 21/265; H01L 21/26513; H01L 29/0626; H01L 29/086; H01L 29/0878; H01L 29/167; H01L 29/4916; H01L 29/51

USPC ................................................... 257/335–345
See application file for complete search history.

(56) References Cited

U.S. PATENT DOCUMENTS

| | | | | |
|---|---|---|---|---|
| 4,149,949 A | * | 4/1979 | Buzza | G01N 33/4925 204/406 |
| 4,361,900 A | * | 11/1982 | Siedband | H05G 1/265 378/111 |
| 6,856,158 B2 | | 2/2005 | Frame et al. | |
| 8,432,174 B2 | * | 4/2013 | Liu | H03M 1/60 324/691 |
| 2002/0022261 A1 | * | 2/2002 | Anderson | B01F 11/0071 435/287.2 |

(Continued)

OTHER PUBLICATIONS

Thirty years of ISFETOLOGY What happened in the past 30 years and what may happen in the next 30 years, P. Bergveld, Jun. 30, 2002, pp. 1-20.

(Continued)

*Primary Examiner* — Daniel Hess
(74) *Attorney, Agent, or Firm* — Cooper Legal Group, LLC

(57) ABSTRACT

One or more circuit arrangements for a biosensor are provided. A circuit arrangement includes an ion sensitive sensor, a differentiator electrically connected to the ion sensitive sensor, an AC signal level comparator electrically connected to the differentiator and a decision circuit electrically connected to the AC signal level comparator. In some embodiments, the AC signal level comparator includes at least one of a first comparator or a second comparator. A method of detecting a bio-reaction is also provided.

20 Claims, 8 Drawing Sheets

(56) References Cited

U.S. PATENT DOCUMENTS

| | | | | |
|---|---|---|---|---|
| 2004/0181728 | A1* | 9/2004 | Pellegrini | G03F 1/144 714/742 |
| 2005/0230271 | A1* | 10/2005 | Levon | G01N 27/4148 205/789 |
| 2009/0251152 | A1* | 10/2009 | Ammann | G01N 27/4163 324/459 |
| 2010/0159461 | A1* | 6/2010 | Toumazou | G01N 27/4148 435/6.11 |
| 2010/0270179 | A1* | 10/2010 | Chou | G01N 27/333 205/787.5 |
| 2012/0001056 | A1* | 1/2012 | Fife | H01L 27/14632 250/208.1 |
| 2012/0043972 | A1 | 2/2012 | Jayaraman | |
| 2013/0002350 | A1* | 1/2013 | Boldt | H03K 5/249 330/253 |
| 2013/0292743 | A1* | 11/2013 | Rothberg | C12Q 1/6874 257/253 |
| 2013/0334578 | A1* | 12/2013 | Huang | G01N 27/4145 257/253 |
| 2014/0209982 | A1* | 7/2014 | Putnam | G01N 27/414 257/253 |
| 2015/0024509 | A1* | 1/2015 | Toumazou | G01N 31/16 436/163 |
| 2015/0129936 | A1 | 5/2015 | Huang et al. | |
| 2015/0308974 | A1* | 10/2015 | Huang | G01N 27/333 257/253 |

OTHER PUBLICATIONS

Label-Free CMOS DNA Quantification With On-Chip Noise Reduction Schemes, Seong-Jin Kim et al., Jun. 2007, pp. 947-950.

An Integrated ISFET Sensor Array, Kazuo Nakazato, Nov. 4, 2009, pp. 8831-8851.

An Intelligent ISFET Sensory System With Temperature and Drift Compensation for Long-Term Monitoring, IEEE Sensors Journal vol. 8, No. 12, D.Y. Chen et al., Dec. 2008, pp. 1948-1959.

An integrated semiconductor device enabling non-optical genome sequencing, Nature10242, vol. 475, Johnathan M. Rothberg et al., Jul. 21, 2011, pp. 348-352.

Research Supplementary Information, Nature 10242, www.nature.com/nature, pp. 1-25.

Optimization of Urea-EnFET Based on $Ta_2O_5$ Layer with Post Annealing, Sensors 2011, Cheng-En Lue et al., pp. 4562-4571.

* cited by examiner

500 →

| Diff-out | cmp1 | cmp2 | Do | Result |
|---|---|---|---|---|
| >Vth1 | 1 | 1 | 1 | There is Bio-Reaction |
| <Vth1 & >Vth2 | 0 | 1 | 0 | No Bio-Reaction |
| <Vth2 | 0 | 0 | 1 | There is Bio-Reaction |

BIOSENSOR DEVICE AND RELATED METHOD

BACKGROUND

The semiconductor industry has experienced rapid growth due to improvements in the integration density of a variety of electronic components (e.g., transistors, diodes, resistors, capacitors, etc.). This improvement in integration density has come, in large part, from shrinking the semiconductor process node. A related aspect of the semiconductor industry similarly experiencing rapid growth is the microelectromechanical systems (MEMS) industry. MEMS devices are found in a variety of applications, ranging from automotive electronics to smartphones, and even biomedical devices.

Biomedical MEMS (BioMEMS) devices perform a variety of functions. A pH sensor is one type of BioMEMS device that electronically determines pH of a solution in contact with the pH sensor. The pH sensor may be used in disease detection, organ tissue monitoring, water contamination identification, or a myriad of other practical applications.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 6 is a truth table for a circuit arrangement of a biosensor in accordance with some embodiments.

DETAILED DESCRIPTION

Figure 1:
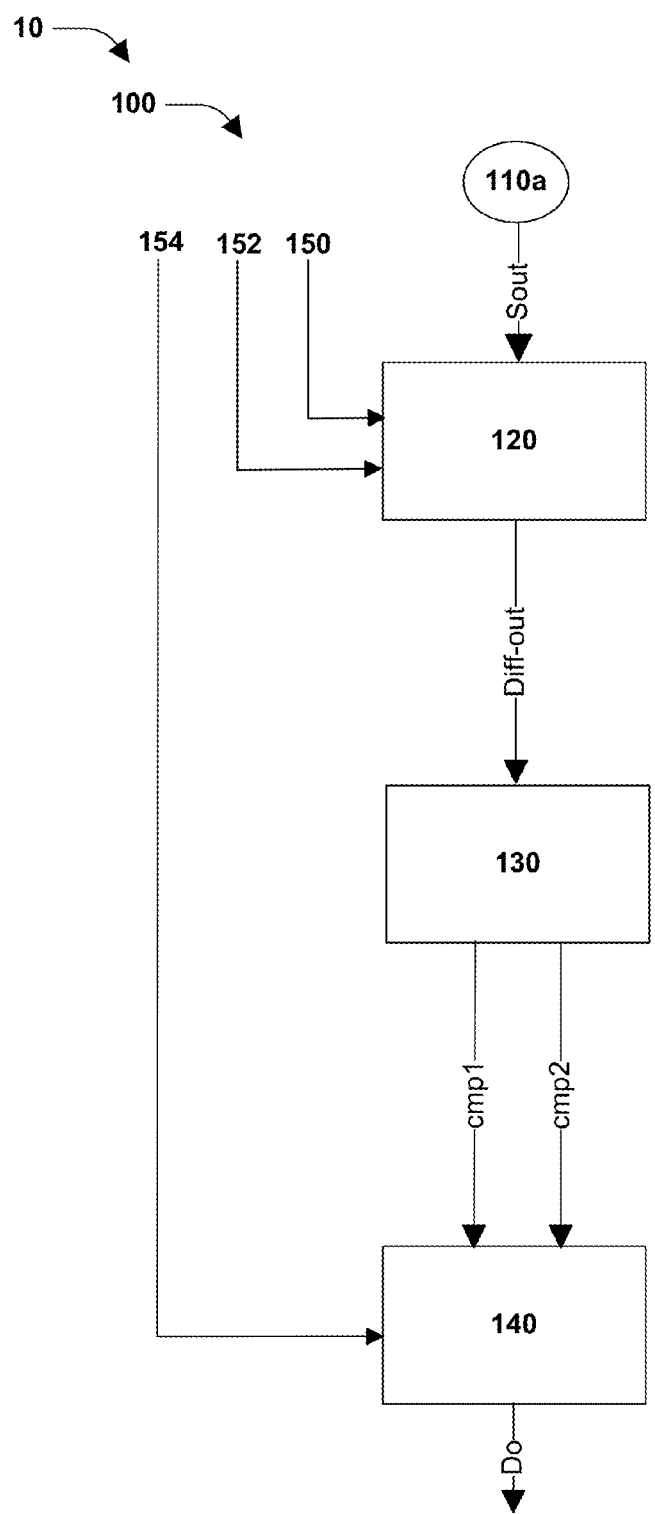
FIG. 1 is an illustration of a circuit arrangement of a biosensor in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

According to some embodiments, one or more circuit arrangements for a biosensor and one or more corresponding methods are provided. In some embodiments, a biosensor is able to directly indicate if a bio-reaction has taken place. In some embodiments, a circuit arrangement is able to mitigate low frequency noise and DC-offset of the biosensor. In some embodiments, the biosensor operates without a calibration phase, and thus does not need a memory cell or the like to store the biosensor's DC-bias or offset.

Turning now to FIG. 1, a diagram of a circuit arrangement 100 of a biosensor 10 in accordance with one or more embodiments is provided. In some embodiments, the circuit arrangement 100 includes at least one of an ion sensitive sensor 110a, a differentiator 120, an AC signal level comparator 130, a decision circuit 140, a sampling clock 150, a reset clock 152 or a latch clock 154. In some embodiments, the circuit arrangement 100 is integrated into a single integrated circuit (IC).

In some embodiments, the ion sensitive sensor 110a is configured to senses a parameter, such as a pH, of a solution, and output a signal, such as a current or voltage. In some embodiments, the ion selective sensor 110a comprises at least one of an ion-sensitive field effect transistor (ISFET), a nanowire or a nanopore. In some embodiments, the ion sensitive sensor 110a includes a converter. In some embodiments, the converter is at least one of a current-to-voltage converter, a voltage-to-current converter, a voltage-to-voltage converter or a capacitance-to-voltage converter. In some embodiments, the converter converts an input signal, such as a current, voltage or capacitance, to a current or voltage.

Figure 2:
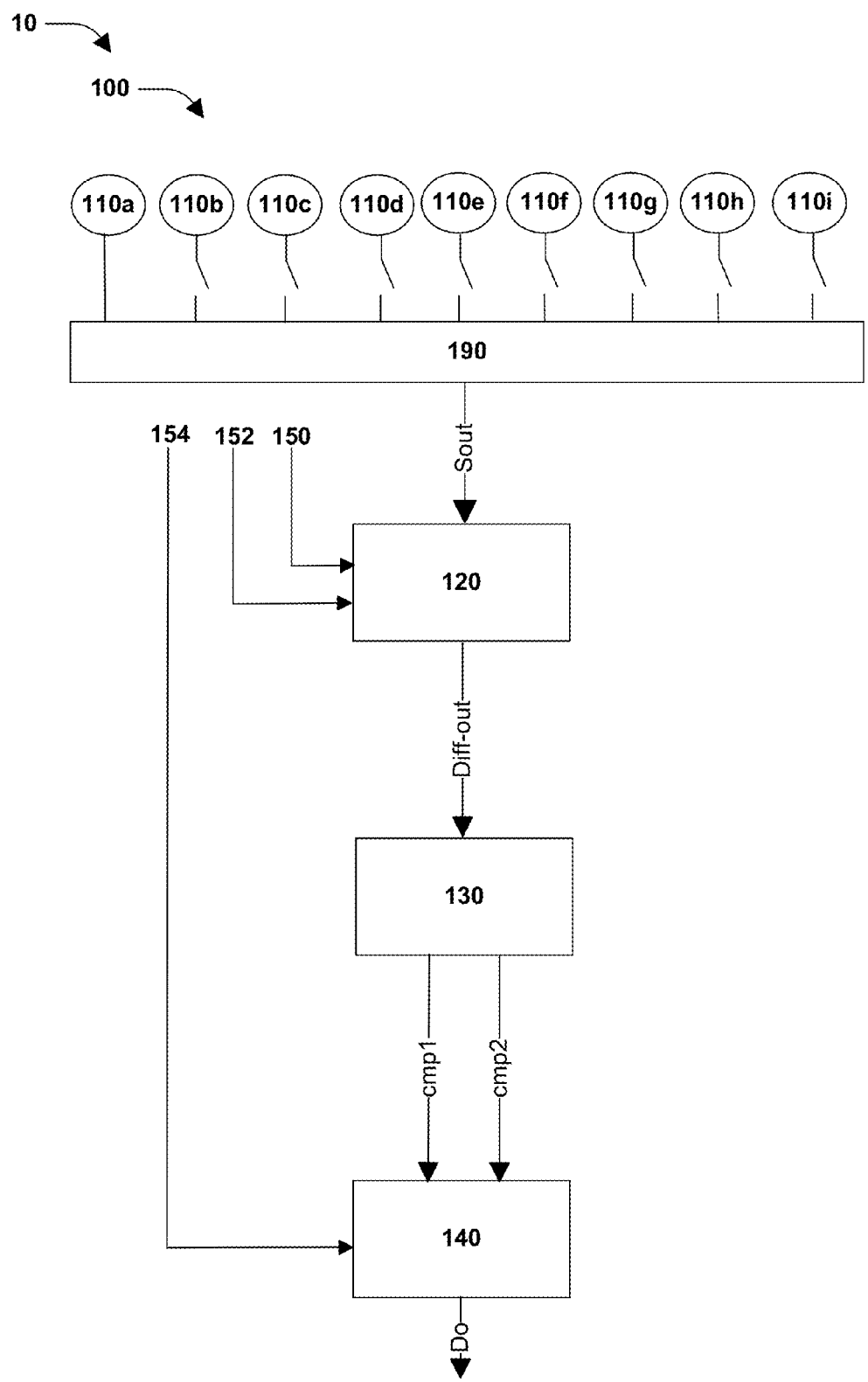
FIG. 2 is an illustration of a circuit arrangement of a biosensor in accordance with some embodiments.

In some embodiments, the ion sensitive sensor 110a is one of an array of ion sensitive sensors 110a-110i, as illustrated in FIG. 2. In some embodiments, at least one of the ion sensitive sensors 110a-110i is connected to a multiplexer 190. In some embodiments, the multiplexer 190 is configured to select at least one of the ion sensitive sensors 110a-110i from the array of ion sensitive sensors. In some embodiments, at least one of the ion sensitive sensors 110a-110i outputs at least one of a first signal out (Sout) or a second Sout. In some embodiments, at least one of the first Sout or the second Sout is at least one of a voltage signal or a current signal. In some embodiments, the first Sout is sensed at a first time and the second Sout is sensed at a second time. In some embodiments, the first Sout and the second Sout are output by the same ion sensitive sensor. In some embodiments, the first Sout and the second Sout are output by different ion sensitive sensors.

In some embodiments, the differentiator 120 is electrically connected to at least one of the ion sensitive sensors 110a-110i. In some embodiments, at least one of the ion sensitive sensors 110a-110i outputs at least one of the first Sout or the second Sout to the differentiator 120. In some embodiments, the differentiator 120 differentiates the first Sout inputted at the first time from the second Sout imputed at the second time. In some embodiments, the differentiator 120 is designed such that an output of the differentiator 120 is approximately directly proportional to a rate of change from the first Sout to the second Sout. In some embodiments, the differentiator 120 differentiates at least one of the first Sout or the second Sout by at least one of a differential voltage or electrical potential (potential), such that in some embodiments at least one of the first Sout is compared to a reference voltage or a common mode voltage (Vcm), such as 156 in FIG. 3, or the second Sout is compared to the reference voltage or the Vcm, such as 156 in FIG. 3. In some embodiments, when the first Sout and the second Sout are at the same potential, the output from the differentiator 120 for the first Sout and the output from the differentiator 120 for the second Sout are equal, such that a differential voltage between the outputs is zero. In some embodiments, when the first Sout and the second Sout have different potentials, the output from the differentiator 120 for the first Sout and the output from the differentiator 120 for the second Sout will differ, such that the differential voltage between the outputs is not zero. In some embodiments, the differentiator 120 amplifies the difference between the output for the first Sout and the output for the second Sout.

Figure 3:
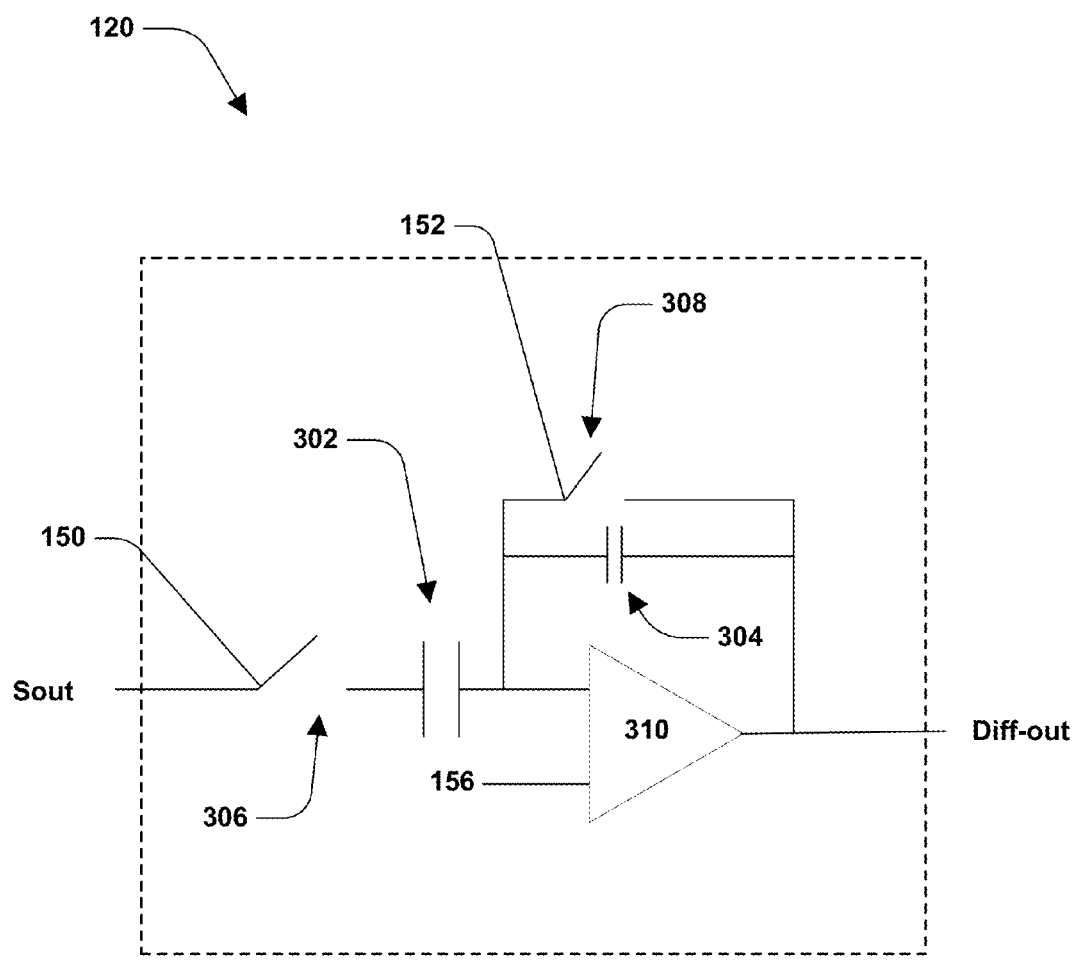
FIG. 3 is an illustration of a circuit arrangement of a biosensor in accordance with some embodiments.

In some embodiments, the differentiator 120 is at least one of an active differentiator or a passive differentiator. In some embodiments, as illustrated in FIG. 3, the differentiator 120 includes at least one of a first capacitor 302, a second capacitor 304, a first switch 306, a second switch 308 or an amplifier 310. In some embodiments, the differentiator 120 is configurable to have at least one of a sampling phase or a reset phase. Referring to FIG. 1, FIG. 2 and FIG. 3, in some embodiments, the sampling phase is controlled by the sampling clock 150 and the reset phase is controlled by the reset clock 152. In some embodiments, at least one of the sampling clock 150 is connected to the first switch 306 or the reset clock 152 is connected to the second switch 308.

In some embodiments, the sampling clock 150 is configured to control the sampling of at least one of the first Sout or the second Sout by the differentiator 120. In some embodiments, the sampling clock 150 will cause the first switch 306 to close initiating the sampling phase. In some embodiments, when the first switch 306 is closed, at least one of the first Sout or the second Sout will flow into at least one of the first capacitor 302, the second capacitor 304 or the amplifier 310. In some embodiments, the Vcm 156 is imputed into the amplifier 310 during the sampling phase, such that the Vcm 156 is compared to at least one of the first Sout or the second Sout.

In some embodiments, the reset clock 152 is configured to reset the differentiator 120. In some embodiments, the reset clock 152 is configured to cause the second switch 308 to close initiating the reset phase. In some embodiments, the reset clock 152 resets the differentiator 120 between a first sampling phase and a second sampling phase. In some embodiments, at least one of the first Sout or the second Sout is stored in the first capacitor 302 during the reset phase. In some embodiments, the charge at the second capacitor 304 is reset to zero during the reset phase. In some embodiments, the reset clock 152 resets the differentiator 120 to the Vcm 156 during the reset phase. In some embodiments, the differentiator 120 will output Vcm 156 during the reset phase.

In some embodiments, the differentiator 120 outputs a differentiator output signal (Diff-out). In some embodiments, the Diff-out is outputted during at least one of the sampling phase or the reset phase. In some embodiments, the Diff-out is directly proportional to the rate of change of the signals inputted into the differentiator 120 during the sampling phase. In some embodiments, the Diff-out is a function of the difference between the first Sout and the Vcm 156 at the first time and the difference between the second Sout and the Vcm 156 at the second time. In some embodiments, the Diff-out reflects a gain of the differentiator 120 where the gain is, according to some embodiments, a function of the Vcm 156 and a charge of the first capacitor 302 divided by a charge of the second capacitor 304. In some embodiments, Diff-out is an AC signal.

Figure 4:
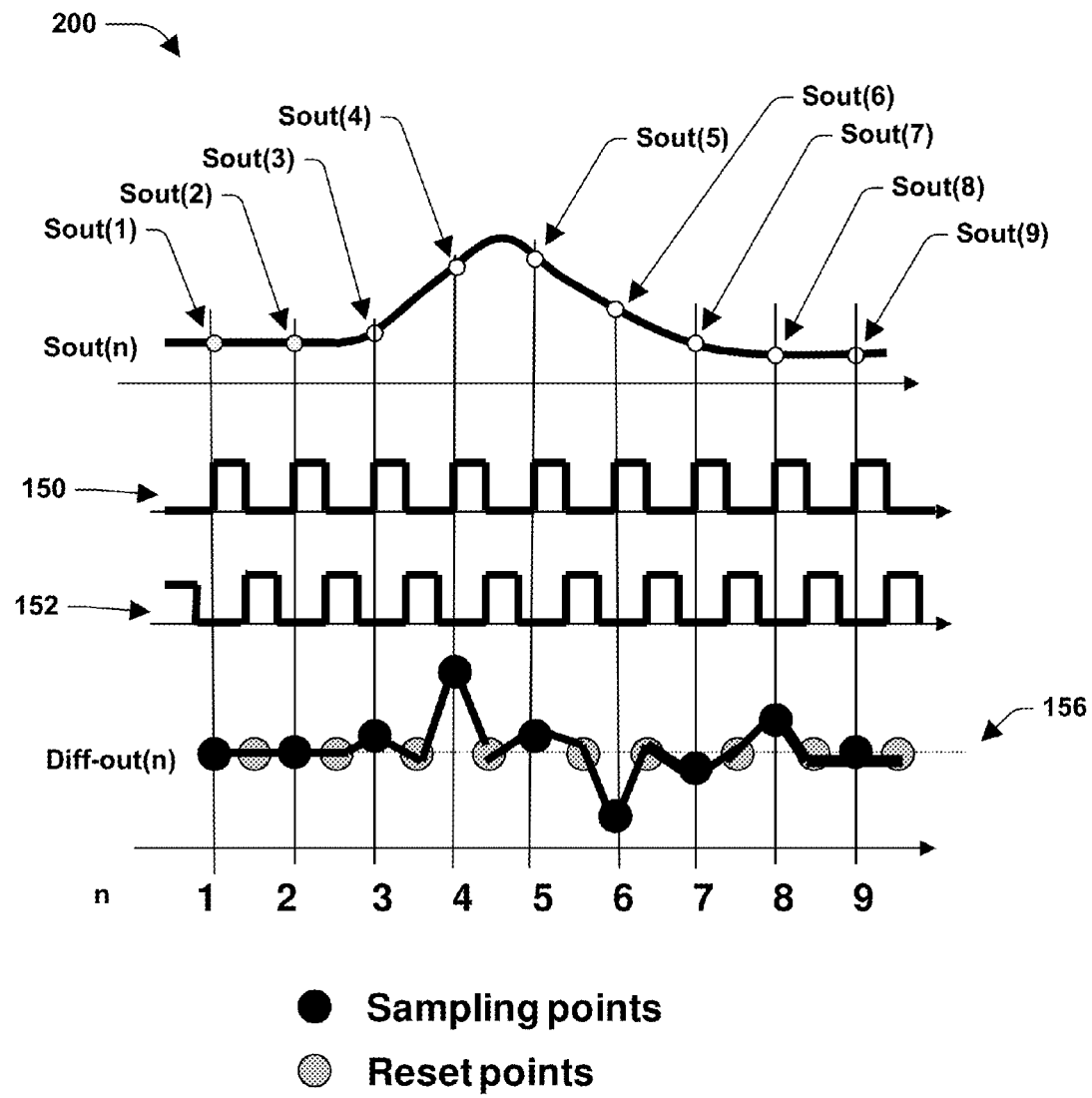
FIG. 4 is an illustration of a timing diagram of a circuit arrangement of a biosensor in accordance with some embodiments.

Turning to FIG. 4, a timing diagram 200 for the differentiator 120 is provided. Referring to FIG. 1, FIG. 2, FIG. 3 and FIG. 4, in some embodiments, the sampling clock 150 will cause the first switch 306 to close initiating the first sampling phase. In some embodiments, during the first sampling phase, the first Sout (Sout(1)) will flow into the differentiator 120. In some embodiments, Diff-out(1) will be outputted. In some embodiments, the reset clock 152 will cause the second switch 308 to close initiating the reset phase. In some embodiments, the reset phase will reset the differentiator 120 to Vcm 156. In some embodiments, during the reset phase the Diff-out will be equal to Vcm 156. In some embodiments, at least one of the sampling clock 150 or the reset clock 152 will cause at least one of the first switch 306 to close or the second switch 308 to open, therein initiating the second sampling phase. In some embodiments, during the second sampling phase, the second Sout (Sout(2)) will flow into the differentiator 120. In some embodiments, a Diff-out(2) will be outputted. In some embodiments, the Diff-out(2) is directly proportional to the rate of change from Sout(1) to Sout(2). In some embodiments, additional signals, such as Sout(3) through Sout(9), are sampled by the differentiator 120 in the same manner described above.

Figure 5:
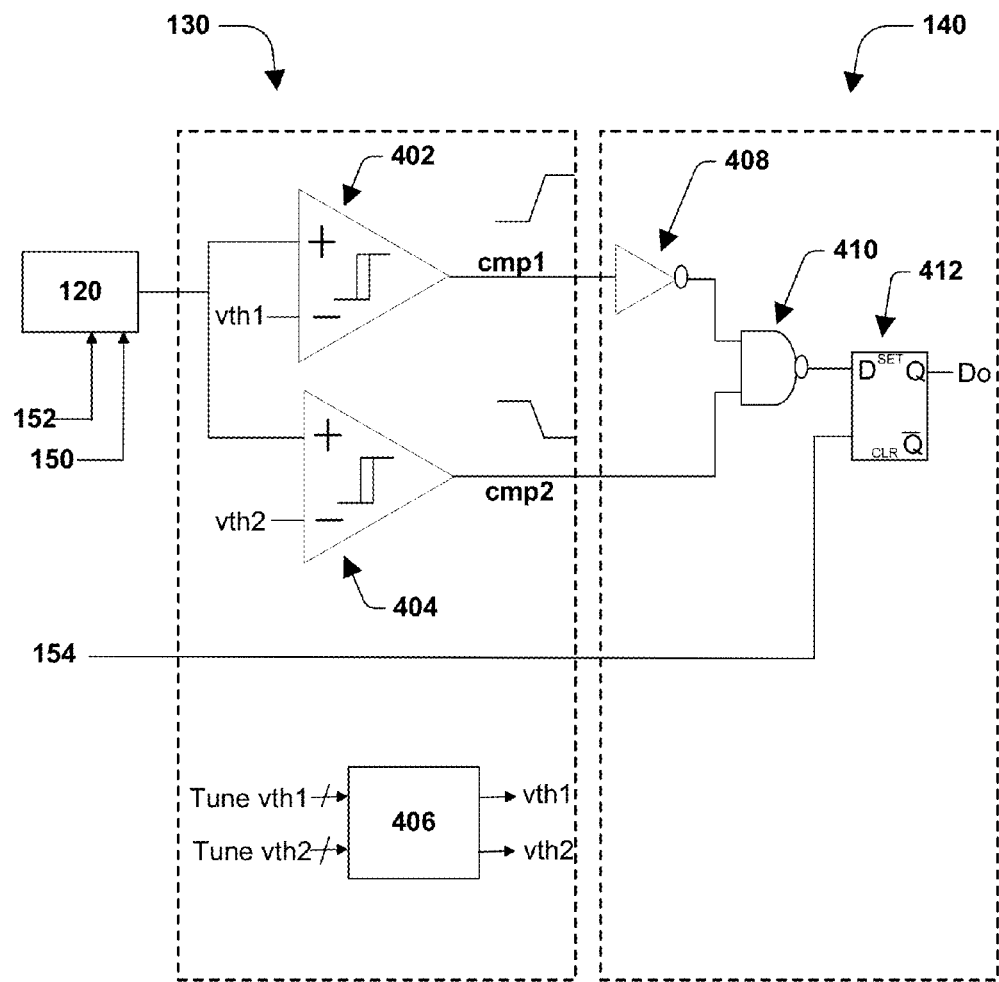
FIG. 5 is an illustration of a circuit arrangement of a biosensor in accordance with some embodiments.

As illustrated in FIG. 5, the AC signal level comparator 130 is electrically connected to the differentiator 120, according to some embodiments. In some embodiments, the AC signal level comparator 130 includes at least one of a first comparator 402, a second comparator 404 or a reference generator 406. In some embodiments, the Diff-out is inputted into at least one of the first comparator 402 or the second comparator 404. In some embodiments, at least one of the first comparator 402 or the second comparator 404 is configured to detect at least one of a positive or a negative AC signal. In some embodiments, at least one of a first threshold voltage (vth1) or a second threshold voltage (vth2) is inputted into at least one of the first comparator 402 or the second comparator 404. In some embodiments, at least one of the first comparator 402 or the second comparator 404 compares at least one of the Diff-outs to at least one of vth1 or vth2. In some embodiments, the AC signal level comparator 130 includes at least one of a third comparator, a fourth comparator or additional comparators (not illustrated).

In some embodiments, the reference generator 406 is configured to generate at least one of vth1 or vth2. In some embodiments, at least one of vth1 or vth2 is set by a first tuning signal (Tune vth1) or a second tuning signal (Tune vth2). In some embodiments, at least one of Tune vth1 or Tune vth2 is a digital signal. In some embodiments, at least one of vth1 or vth2 is at least one of a positive threshold level or a negative threshold level. In some embodiments, the positive threshold level is between about 0.01 v to about 1 v. In some embodiments, the negative threshold level is between about −0.01 v to about −1 v.

In some embodiments, at least one of the first comparator 402 or the second comparator 404 outputs at least one of a first comparator output (cmp1) or a second comparator output (cmp2). In some embodiments, at least one of cmp1 or cmp2 is a function of whether Diff-out is greater or less than at least one of vth1 or the vth2. In some embodiments, at least one of cmp1 or cmp2 is inverted by an inverter 408.

In some embodiments, the decision circuit 140 is electrically connected to the AC signal level comparator 130. In some embodiments, the decision circuit 140 is a logic circuit. In some embodiments, the decision circuit 140 includes at least one of a nand gate 410 or a latch 412. In some embodiments, at least one of cmp1 or cmp2 is imputed into the nand gate 410. In some embodiments, a nand output (No) is inputted into the latch 412. In some embodiments, the latch 412 is configured to output a one bit signal (Do) to indicate whether or not there is a bio-reaction. In some embodiments, the latch clock 154 is connected to the latch 412. In some embodiments, the latch 412 comprises a DQ flip-flop. In some embodiments, the latch clock 154 is synchronized with the sampling clock 150. In some embodiments, the latch 142 is configured to latch the result through the latch clock 154. In some embodiments, the decision circuit 140 includes additional nand gates (not illustrated) connected to at least one of the additional comparator(s) (not illustrated).

In some embodiments, the decision circuit 140 is associated with or operates according to a truth table 500, illustrated in FIG. 6. In some embodiments, if the Diff-out is greater than vth1 then the first comparator 402 and the second comparator 404 will both output 1 and the decision circuit 140 will output 1 indicative that a bio-reaction was sensed. In some embodiments, if the Diff-out is less than vth1 but greater than vth2 then the first comparator 402 will output 0 and the second comparator 404 will output 1 and the decision circuit 140 will output 0 indicative that no bio-reaction was sensed. In some embodiments, if the output of the differentiator 120 is less than vth2 then the first comparator 402 and the second comparator 404 will output 0 and the decision circuit 140 will output 1 indicative of a bio-reaction being sensed. In some embodiments, an output from each of the ion sensitive sensors 110a-110i is used to directly indicate whether there is a bio-reaction or not using at least one of the differentiator 120, AC signal level comparator 130 or decision circuit 140.

In some embodiments, at least one of low frequency noise, long-term drift, ion diffusion, or pixel-to-pixel crosstalk associated with an ion sensitive sensor 110 is mitigated by implementing at least one of the differentiator 120, AC signal level comparator 130 or decision circuit 140. In some embodiments, low frequency noise is mitigated without the need for a memory cell or a quantizer.

Figure 7:
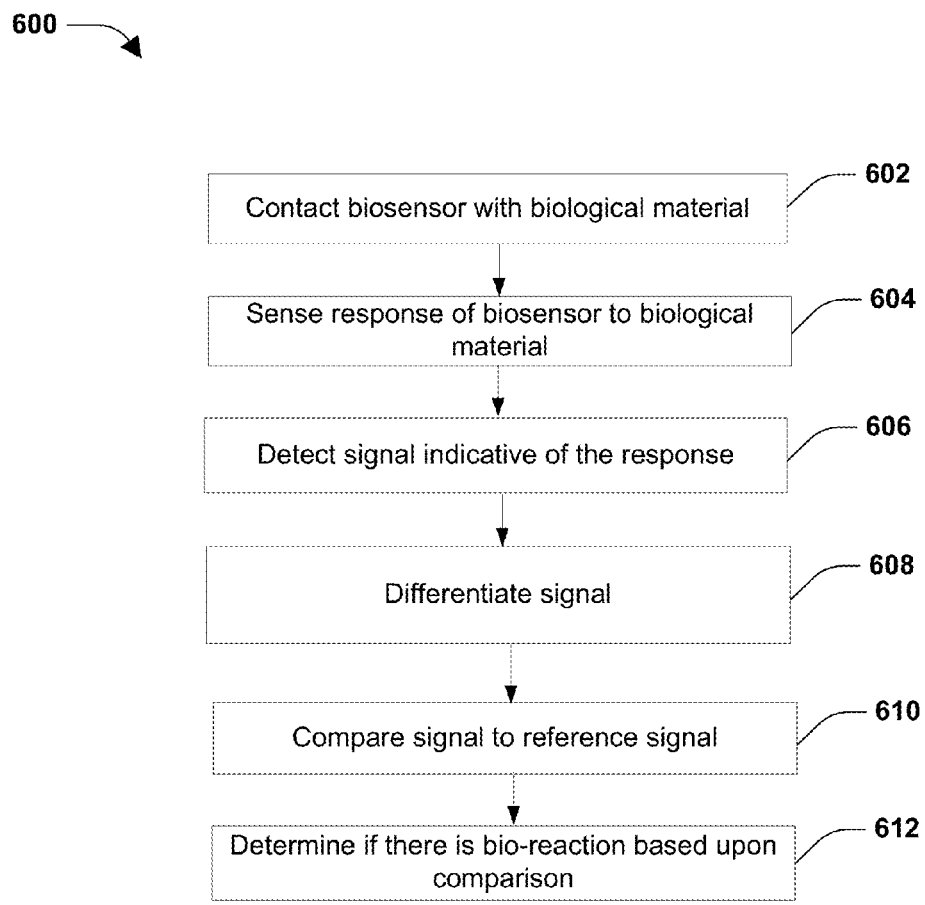
FIG. 7 is a flow diagram illustrating a method for sensing a bio-reaction in accordance with some embodiments.

Referring to FIG. 7, illustrated is a flow diagram of a method 600 for sensing a bio-reaction according to some embodiments. In some embodiments, additional processes are provided at least one of before, during, or after the method 600 of FIG. 7. At 602, a biological material is brought into contact with a biosensor, such as biosensor 10. In some embodiments, the biological material is brought into contact with an ion sensitive sensor, such as 110a, of the biosensor 10. In some embodiments, the biological material contacts a gate of an ISFET. In some embodiments, the biological material is provided in a liquid form. At 604, a response of the biosensor to the biological material is sensed. In some embodiments, the biological material contacting the gate of the ISFET changes the threshold voltage of the ISFET, and alters an output current or voltage of the ISFET. At 606, a signal indicative of a response is detected. In some embodiments, the signal is at least one of a voltage signal or a current signal. In some embodiments, the signal is an AC signal. At 608, the signal is differentiated. In some embodiments, a difference between a first signal and a second signal is adjusted by a gain in differentiating the signal. At 610, the signal is compared to a first reference signal. In some embodiments, the signal is compared to a second reference signal. In some embodiments, at least one of the first reference signal or the second reference signal is a threshold voltage. In some embodiments, at least one of the first reference signal or the second reference signal is tuned to a desired threshold voltage. At 612, a determination is made as to whether a bio-reaction occurred based upon the comparison. In some embodiments, a decision circuit 140 is used to determine if there is a bio-reaction. In some embodiments, the decision circuit 140 directly shows if there is a bio-reaction or not.

Figure 8:
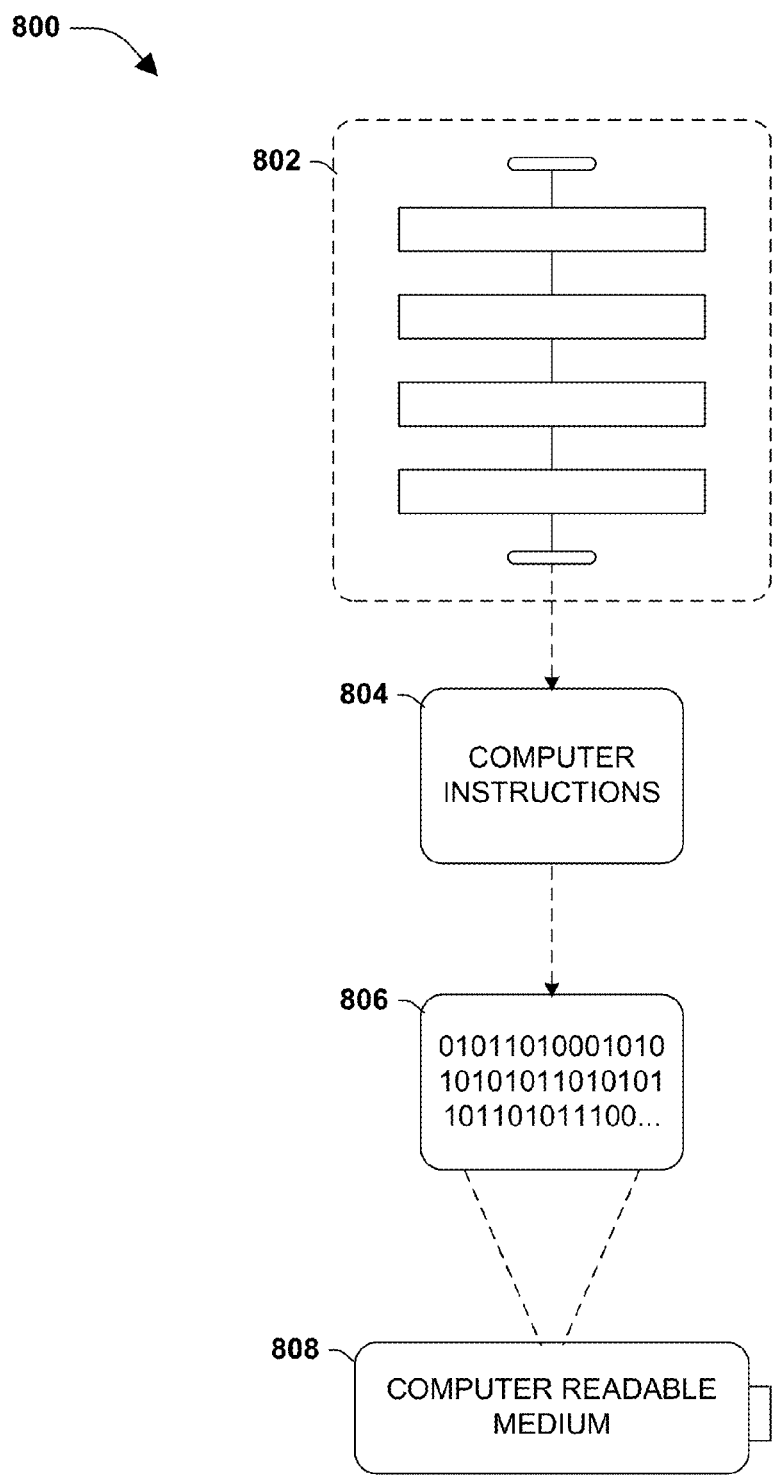
FIG. 8 is an illustration of an exemplary computer readable medium wherein processor-executable instructions configured to embody one or more of the provisions set forth herein may be comprised.

Still another embodiment involves a computer-readable medium comprising processor-executable instructions configured to implement one or more of the techniques presented herein. An example embodiment of a computer-readable medium or a computer-readable device is illustrated in FIG. 8, wherein the implementation 800 comprises a computer-readable medium 808, such as a CD-R, DVD-R, flash drive, a platter of a hard disk drive, etc., on which is encoded computer-readable data 806. This computer-readable data 806, such as binary data comprising at least one of a zero or a one, in turn comprises a set of computer instructions 804 configured to operate according to one or more of the principles set forth herein. In some embodiments, the processor-executable computer instructions 804 are configured to perform a method 802, such as at least some of the exemplary method 600 of FIG. 7, for example. Many such computer-readable media are configured to operate in accordance with the techniques presented herein.

According to some aspects of the instant disclosure, a circuit arrangement is provided. The circuit arrangement comprises an ion sensitive sensor, a differentiator electrically connected to the ion sensitive sensor, an AC signal level comparator electrically connected to the differentiator and a decision circuit electrically connected to the AC signal level comparator.

According to some aspects of the instant disclosure, a circuit arrangement is provided. The circuit arrangement comprises an ion sensitive sensor, a differentiator electrically connected to the ion sensitive sensor, an AC signal level comparator electrically connected to the differentiator and a decision circuit electrically connected to the AC signal level comparator. The AC signal level comparator comprising a first comparator. The decision circuit comprising a nand gate.

According to some aspects of the instant disclosure, a method is provided. The method comprising contacting a biosensor with a biological material, sensing a response of the biosensor to the biological material by a ion sensitive sensor, detecting a signal indicative of the response, differentiating the signal, comparing the signal to a reference signal and determining if there is a bio-reaction based upon the comparison.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

Various operations of embodiments are provided herein. The order in which some or all of the operations are described should not be construed as to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Further, unless specified otherwise, "first," "second," or the like are not intended to imply a temporal aspect, a spatial aspect, an ordering, etc. Rather, such terms are merely used as identifiers, names, etc. for features, elements, items, etc. For example, a first channel and a second channel generally correspond to channel A and channel B or two different or two identical channels or the same channel.

It will be appreciated that layers, features, elements, etc. depicted herein are illustrated with particular dimensions relative to one another, such as structural dimensions or orientations, for purposes of simplicity and ease of understanding and that actual dimensions of the same differ substantially from that illustrated herein, in some embodiments.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B or the like generally means A or B or both A and B. Furthermore, to the extent that "includes", "having", "has", "with", or variants thereof are used in either the detailed description or the claims, such terms are intended to be inclusive in a manner similar to the term "comprising".

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A circuit arrangement comprising:
an ion sensitive sensor;
a differentiator electrically connected to the ion sensitive sensor, wherein the differentiator comprises:
a first capacitor; and
an amplifier;
an AC signal level comparator electrically connected to the differentiator; and
a decision circuit electrically connected to the AC signal level comparator.

2. The circuit arrangement of claim 1, comprising:
an array of ion sensitive sensors.

3. The circuit arrangement of claim 2, comprising:
a multiplexer electrically connected to the array of ion sensitive sensors.

4. The circuit arrangement of claim 1, wherein the ion sensitive sensor is an ion-sensitive field effect transistor (ISFET).

5. The circuit arrangement of claim 1, wherein the decision circuit comprises:
a nand gate; and
a latch.

6. The circuit arrangement of claim 1, wherein the AC signal level comparator comprises:
a first comparator; and
a second comparator.

7. The circuit arrangement of claim 6, wherein the AC signal level comparator comprises:
an inverter, the inverter electrically connected to at least one of the first comparator or the second comparator.

8. The circuit arrangement of claim 1, wherein the AC signal level comparator comprises:
a reference signal tuner.

9. The circuit arrangement of claim 1, wherein the first capacitor is electrically connected to a first input terminal of the amplifier.

10. The circuit arrangement of claim 1, comprising:
a second capacitor disposed between a first input terminal and an output terminal of the amplifier.

11. A circuit arrangement comprising:
a ion sensitive sensor;
a differentiator electrically connected to the ion sensitive sensor, wherein the differentiator comprises:
a first capacitor;
a second capacitor;
a first switch;
a second switch; and
an amplifier;
an AC signal level comparator electrically connected to the differentiator, the AC signal level comparator comprising:
a first comparator; and
a decision circuit electrically connected to the AC signal level comparator, the decision circuit comprising:
a nand gate.

12. The circuit arrangement of claim 11, wherein the ion sensitive sensor is an ion-sensitive field effect transistor (ISFET).

13. The circuit arrangement of claim 11, wherein the decision circuit comprises:
a latch.

14. The circuit arrangement of claim 11, wherein the AC signal level comparator comprises:
a second comparator.

15. The circuit arrangement of claim 14, wherein the AC signal level comparator comprises:
an inverter, the inverter electrically connected to at least one of the first comparator or the second comparator.

16. The circuit arrangement of claim 11, wherein the AC signal level comparator comprises:
a reference signal tuner.

17. The circuit arrangement of claim 11, comprising:
an array of ion sensitive sensors.

18. A circuit arrangement comprising:
an ion sensitive sensor configured to generate an output based upon a pH of a solution to which the ion sensitive sensor is exposed;
a differentiator electrically connected to the ion sensitive sensor and comprising:
a switch configured to selectively couple the output of the ion sensitive sensor to a capacitor;

an amplifier configured to compare the output of the ion sensitive sensor to a reference signal, the capacitor disposed between the switch and a first input terminal of the amplifier;

a second capacitor disposed between the first input terminal and an output terminal of the amplifier; and a second switch in parallel with the second capacitor, wherein an output of the amplifier is reset based upon the reference signal responsive to the second switch being closed;

an AC signal level comparator electrically connected to the differentiator; and a decision circuit electrically connected to the AC signal level comparator.

19. The circuit arrangement of claim 18, the AC signal level comparator comprising:

a first comparator having a third input terminal electrically connected to the output terminal of the amplifier and a fourth input terminal electrically connected to a reference generator configured to apply a second reference signal to the fourth input terminal; and a second comparator having a fifth input terminal electrically connected to the output terminal of the amplifier and a sixth input terminal electrically connected to a second reference generator configured to apply a third reference signal to the sixth input terminal.

20. The circuit arrangement of claim 19, wherein the second reference signal corresponds to a positive voltage reference signal and the third reference signal corresponds to a negative voltage reference signal.

* * * * *